US009873531B2

(12) United States Patent
Chu (10) Patent No.: US 9,873,531 B2
(45) Date of Patent: Jan. 23, 2018

(54) SYSTEM FOR PACKAGING AND DISPENSING DISPOSABLE ELASTOMERIC GLOVES

(71) Applicant: Donald L. Chu, Long Valley, NJ (US)

(72) Inventor: Donald L. Chu, Long Valley, NJ (US)

(73) Assignee: TRONEX INTERNATIONAL INCORPORATED, Mt. Olive, NJ (US)

( * ) Notice: Subject to any disclaimer, the term of this patent is extended or adjusted under 35 U.S.C. 154(b) by 352 days.

(21) Appl. No.: 14/339,936

(22) Filed: Jul. 24, 2014

(65) Prior Publication Data

US 2016/0023838 A1    Jan. 28, 2016

(51) Int. Cl.
| B65H 1/00 | (2006.01) |
|---|---|
| B65B 7/26 | (2006.01) |
| B65D 83/08 | (2006.01) |
| B65B 25/20 | (2006.01) |
| A61B 50/20 | (2016.01) |
| A61B 42/40 | (2016.01) |
| B65B 5/06 | (2006.01) |
| A61B 50/30 | (2016.01) |
| B65B 35/50 | (2006.01) |
| B65B 63/04 | (2006.01) |

(52) U.S. Cl.
CPC ............. B65B 7/26 (2013.01); A61B 42/40 (2016.02); A61B 50/20 (2016.02); B65B 25/20 (2013.01); B65D 83/0805 (2013.01); *A61B 2050/314* (2016.02); *B65B 5/067* (2013.01); *B65B 35/50* (2013.01); *B65B 63/04* (2013.01); *B65B 2220/18* (2013.01); *Y02W 30/807* (2015.05)

(58) Field of Classification Search
CPC   B65B 7/26; B65B 25/20; B65B 5/067; B65B 35/50; B65B 63/04; B65B 2220/18; A61B 42/40; A61B 50/20; A61B 2050/314; Y02W 30/807
USPC ............................................................ 221/33
See application file for complete search history.

(56) References Cited

U.S. PATENT DOCUMENTS

| 4,436,231 A * | 3/1984 | Kelly .................. A41D 19/043 223/40 |
|---|---|---|
| 5,096,089 A | 3/1992 | McLaughlin |
| 5,562,229 A * | 10/1996 | Callahan ................ A47G 29/06 150/154 |
| 5,628,858 A * | 5/1997 | Petrou ...................... B65C 1/00 156/247 |

(Continued)

FOREIGN PATENT DOCUMENTS

WO    WO2011017496 A2    2/2011

*Primary Examiner* — Rakesh Kumar (74) *Attorney, Agent, or Firm* — Thomas J. Germinario (57) ABSTRACT

An integrated method packages and dispenses three-dimensional disposable elastomeric gloves that are easy to put on, comfortable to wear and do not interfere with manual and/or digital movements. The three-dimensional gloves are integrated with a dispensing system that employs both bags and re-usable dispenser boxes, as well as visible glove labelling. The glove bags are accessed through slits that can be an overlapping edge or a cut slit, or of a perforated or peel-back type, and the latter can also be re-sealable for storage purposes. Once filled with randomly-stacked three-dimensional gloves, the bags are placed in dispenser boxes made of a rigid plastic or metal, with the bag slits being aligned with access apertures of the dispenser boxes.

7 Claims, 9 Drawing Sheets

(56) References Cited

U.S. PATENT DOCUMENTS

| | | | |
|---|---|---|---|
| 5,921,434 A | | 7/1999 | Hollander et al. |
| 6,062,421 A | | 5/2000 | Marley |
| 6,112,936 A | * | 9/2000 | Arizmendi ......... B65D 83/0805 150/154 |
| RE37,164 E | * | 5/2001 | Petrou ..................... B65C 1/00 156/247 |
| 7,866,507 B2 | * | 1/2011 | Sawin .................. B65D 25/205 206/216 |
| 7,975,455 B1 | * | 7/2011 | Abrahamsen ........... B65B 7/167 53/428 |
| 2003/0057222 A1 | * | 3/2003 | Milliorn ................. B65D 77/06 221/46 |
| 2004/0099623 A1 | | 5/2004 | Kurtz et al. |
| 2005/0015846 A1 | * | 1/2005 | Vistins .................... B29C 41/14 2/161.7 |
| 2005/0271842 A1 | * | 12/2005 | Triebes .............. A41D 19/0058 428/35.7 |
| 2008/0061073 A1 | * | 3/2008 | Laroche ............... A47K 10/421 221/46 |
| 2008/0064278 A1 | * | 3/2008 | Oaroche ................ A47K 10/16 442/59 |
| 2008/0311409 A1 | * | 12/2008 | Lipinski ................. B29C 33/64 428/451 |
| 2015/0232216 A1 | * | 8/2015 | Stollery ................. B65B 35/50 53/436 |
| 2016/0023838 A1 | * | 1/2016 | Chu .......................... B65B 7/26 221/1 |

\* cited by examiner

SYSTEM FOR PACKAGING AND DISPENSING DISPOSABLE ELASTOMERIC GLOVES

FIELD OF INVENTION

The present invention relates to the field of disposable elastomeric gloves, and more particularly to methods of packaging and dispensing disposable elastomeric gloves.

BACKGROUND OF THE INVENTION

Existing disposable elastomeric gloves, often made of polyethylene-based plastics, are in wide use for such purposes as food service and medical examination. Such gloves typically have a flat, two-dimensional form created by a punching and heat-sealing process. The flatness of these gloves allows them to be dispensed from a disposable cardboard box with a tearable access panel, similar to boxes for dispensing facial tissues. Even where non-disposable dispensers are used, their dispensing mechanisms rely on the flat, uniform stacking of the gloves.

This existing elastomeric glove packaging and dispensing technology is less than optimal for several reasons. Employing non-reusable/disposable boxes creates additional packaging waste, the cardboard absorbs moisture and does not provide hygienic protection for the gloves, and the perforated opening also absorbs dirt, moisture and bacteria. While the use of non-disposable dispenser boxes helps minimize packaging waste, they lack the labelling of cardboard boxes, which usually identify the glove by size, type, unit count, etc.

Therefore, an unmet need exists for a method of packaging three-dimensional disposable elastomeric gloves that is integrated with a cooperating method of effectively dispensing such gloves from a reusable dispenser which provides visibility for labelling of glove information and/or specifications. The principal objective of the present invention is to fulfill this need.

SUMMARY OF THE INVENTION

The present invention is an integrated method of packaging and dispensing three-dimensional disposable elastomeric gloves that are easy to put on, comfortable to wear and do not interfere with manual and/or digital movements. The three-dimensional gloves are integrated with a dispensing system that employs both bags and re-usable dispenser boxes, as well as visible glove labelling.

Instead of the punching and heat-sealing process used to make flat, two-dimensional, polyethylene-based gloves, the disposable gloves of the present invention are fabricated by dipping a hand-shaped mold into a liquid resin of elastomeric material, such as nitrile, vinyl or latex. The gloves are cured on the mold and then peeled off to produce a three-dimensional glove form.

While two-dimensional gloves are stacked flat with a uniform orientation—i.e., with fingers and thumbs all aligned in the same direction—the three-dimensional gloves of the present invention are stacked with random orientations and placed in a transparent plastic bag. Such random stacking causes the gloves to become slightly entangled, so that pulling an upper glove from the bag frictionally draws the glove beneath it toward the bag opening. This feature obviates the need for complex dispensing mechanisms that are required for two-dimensional, flat-stacked gloves.

The bagged gloves are accessed through narrow oblong slit openings that can be, for example, a perforated opening, an overlapping edge or a cut slit, or a peel-back opening, where the latter can also be re-sealable for storage purposes. Once filled with randomly-stacked three-dimensional gloves, the bags are typically shipped to the end user in cardboard boxes containing multiple bags. The bags are placed by the end user into dispenser boxes made of a rigid plastic or metal, with the bag openings being aligned with access apertures of the dispenser boxes.

Preferably, the glove bags have labels that identify the gloves by material, type, size and/or unit count. The visibility of the bag labels can be achieved by making one or more of the walls of the dispenser boxes transparent, or by aligning the labels with cooperating apertures in the dispenser boxes. Alternately, the labels can be detachable from the bags and re-attachable to the dispenser box. For example, the label can slide into a pair of tracks, slots or grooves in the top of the dispenser box.

Access to the dispenser box for inserting the glove bag can be through an open side or missing wall of the box, through a sliding top or side box panel, or through a hinged box top or side. Once a glove bag has been emptied, it is replaced within the dispenser box by another bag. If the replacement gloves are of a different type, material, size or unit count, detachable labels, if any, can be replaced on the dispenser box.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENT

Figure 1:
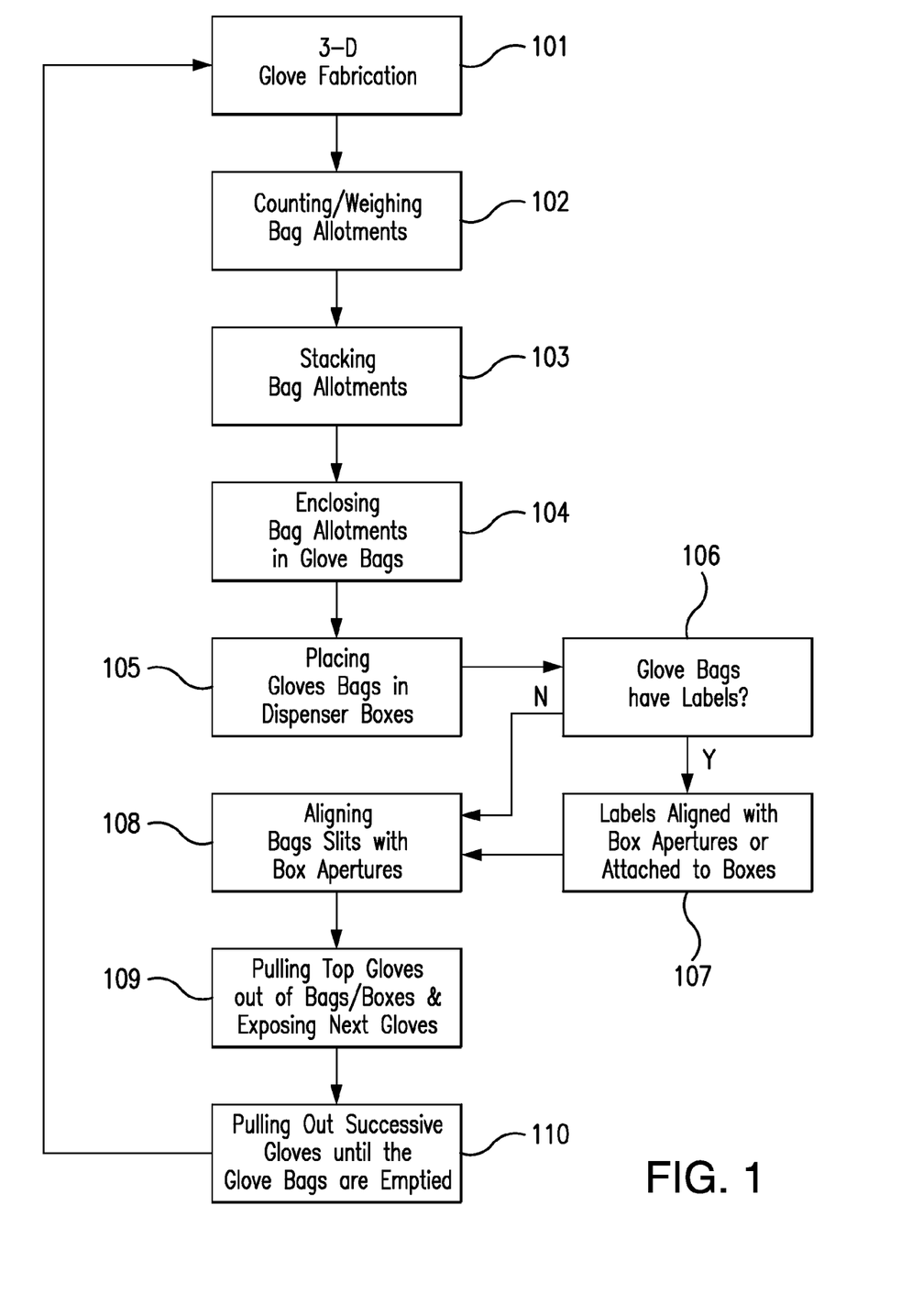
FIG. 1 is a flow chart depicting the steps comprising a method of producing and dispensing disposable gloves according to one embodiment of the present invention.
Figure 2:
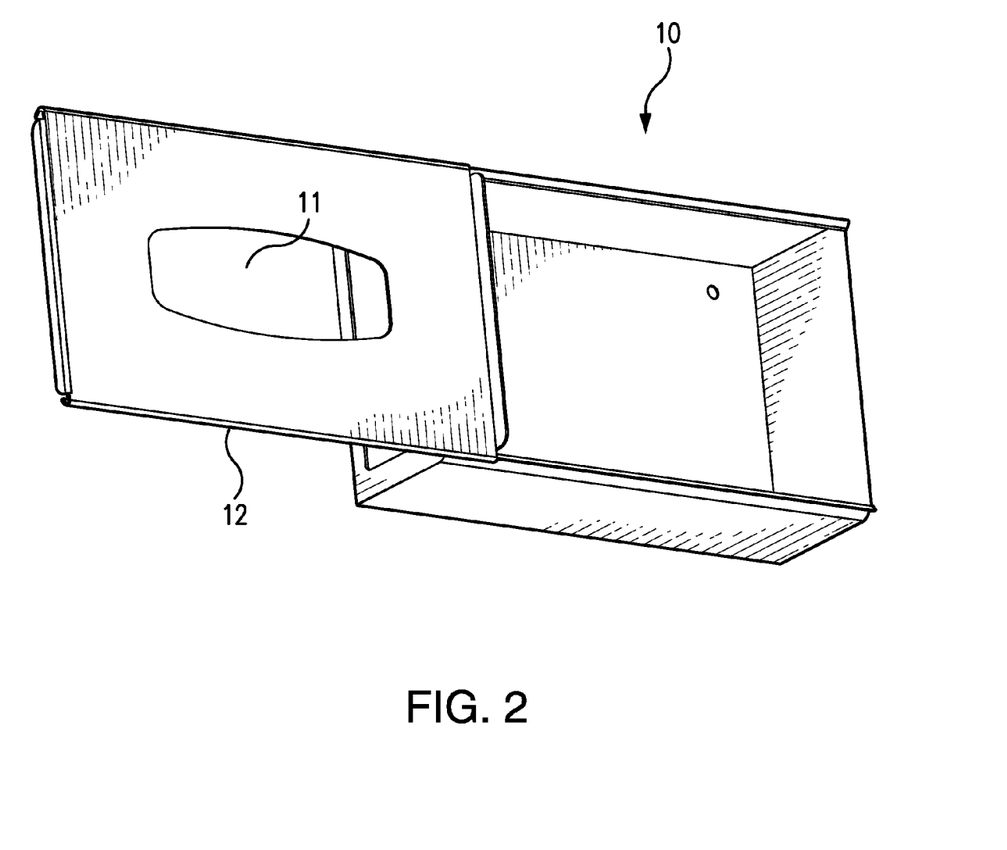
FIG. 2 is a perspective view of a dispenser box having a slidable access lid, which is opened to enable insertion of a glove bag within the box.

Referring to FIG. 1, the preferred method of packaging and dispensing disposable gloves comprises the following steps:

101: fabricating each of the disposable gloves by dipping a hand-shaped mold into a liquid resin of an elastomeric material, such as latex, vinyl or nitrile, curing the resin on the mold, and then peeling off the glove, such that each glove has a three-dimensional form;

102: counting or weighing groups of the gloves so as to constitute multiple bag allotments, wherein each bag allotment contains a specified number of gloves all of one specified material, size and thickness;

103: stacking the gloves of each bag allotment one on top of another, so as to constitute a bag allotment stack, wherein each bag allotment stack comprises a top glove, a bottom glove, and multiple successive gloves between the top glove and the bottom glove;

104: enclosing each bag allotment stack within a glove bag, wherein each glove bag comprises a flexible sheet or film of plastic defining an interior bag space, and wherein the interior bag space is accessible through one or more bag slits, which are narrow oblong openings;

105: placing each glove bag within a dispenser box, wherein each dispenser box comprises four or more substantially rectangular, rigid plastic dispenser walls defining an interior dispenser space, and wherein the interior dispenser space is accessible through one or more box apertures in one or more of the dispenser walls;

106: if the glove bags have labels, either 107 aligning one or more of the bag labels with one of the box apertures, so that the bag labels are visible through the aligned box aperture, or detaching one or more of the bag labels from the glove bag and attaching one or more of the glove labels to one or more of the dispenser walls, such that the attached bag labels are visible on the dispenser walls;

108: aligning at least one of the bag slits with one of the box apertures;

109: pulling out the top glove from the glove bag through the bag slit and then through the aligned box aperture, and thereby exposing, by friction and entanglement between the gloves, a next successive glove at the bag slit; and 110: pulling each successive glove from the glove bag through the bag slit and then through the aligned box aperture, and thereby exposing, by friction and entanglement between the gloves, a next successive glove at the bag slit, until the bottom glove is pulled out and the glove bag is empty.

Figure 3:
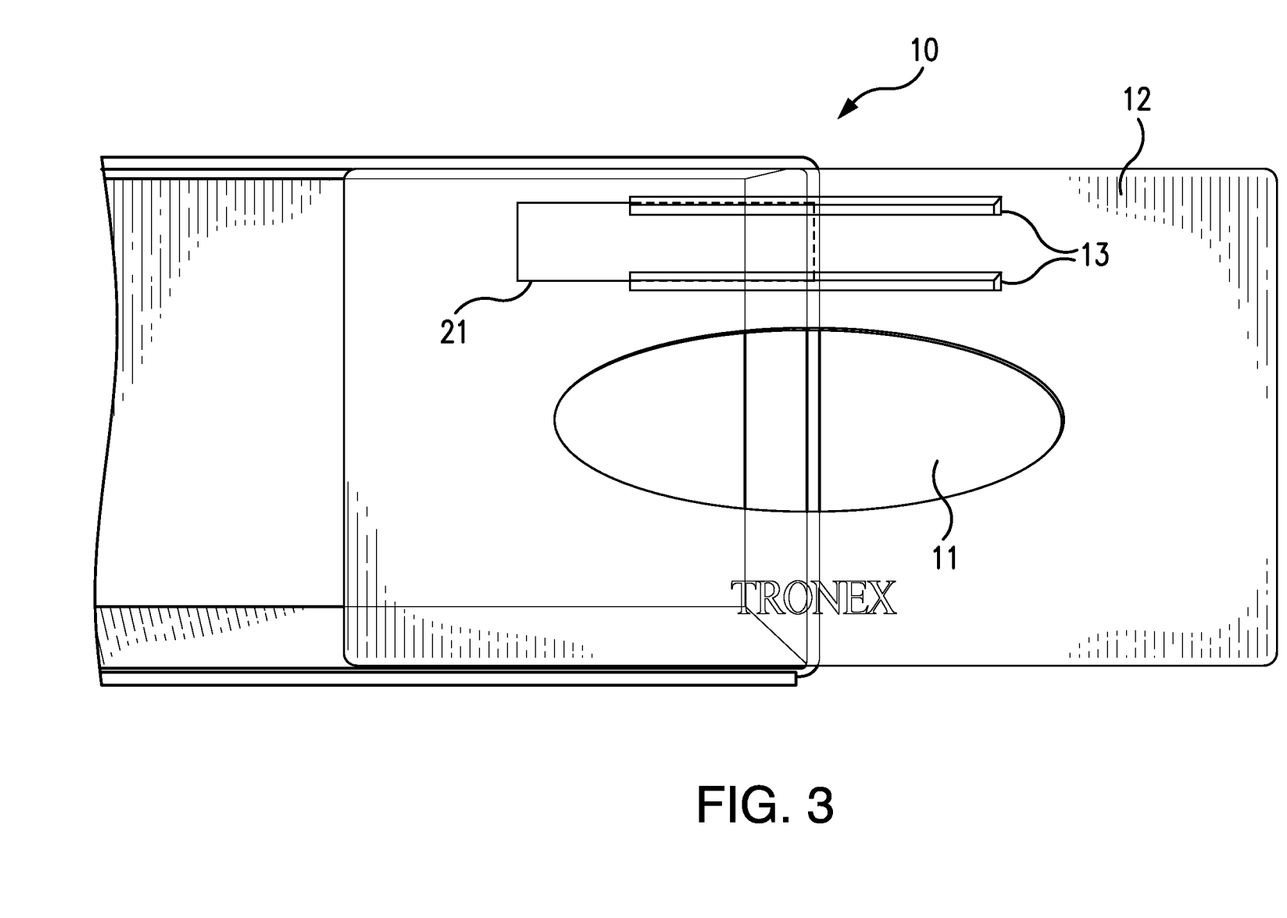
FIG. 3 is a top plan view of a dispenser box having a slidable access lid with cooperating dual tracks for insertion of a glove bag label.
Figure 4:
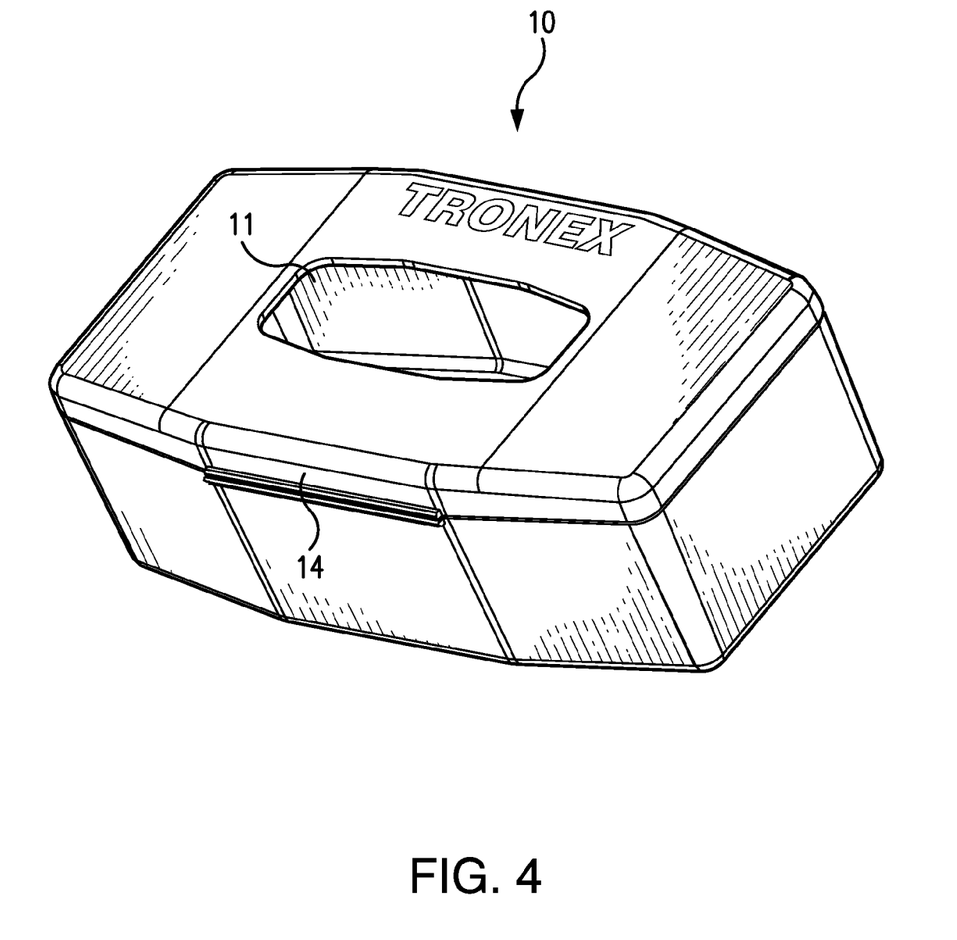
FIG. 4 is a perspective view of a dispenser box having a hinged access lid, which can be opened to enable insertion of a glove bag within the box.
Figure 5:
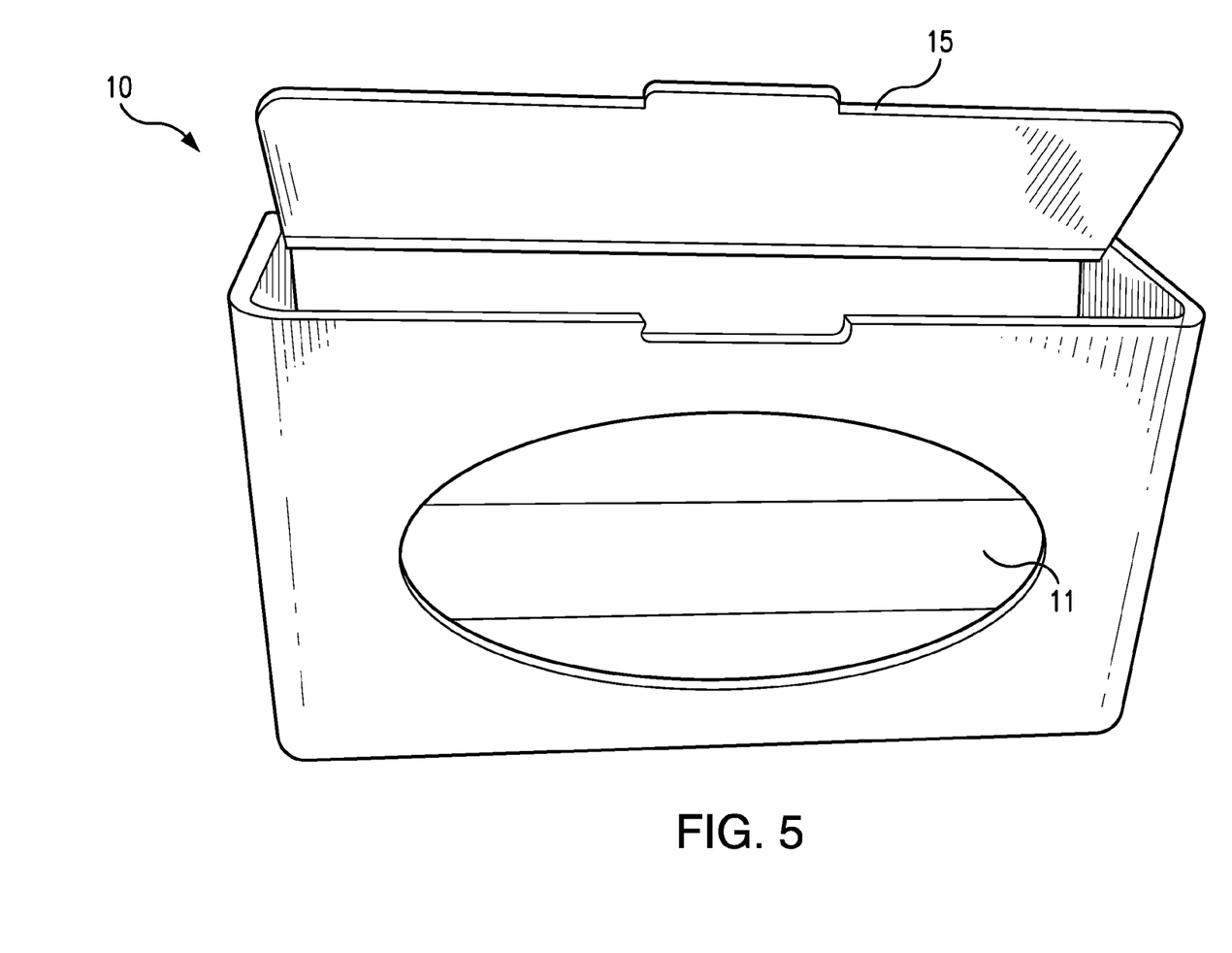
FIG. 5 is a perspective view of a dispenser box having a hinged side wall, which is opened to enable insertion of a glove bag within the box.
Figure 6:
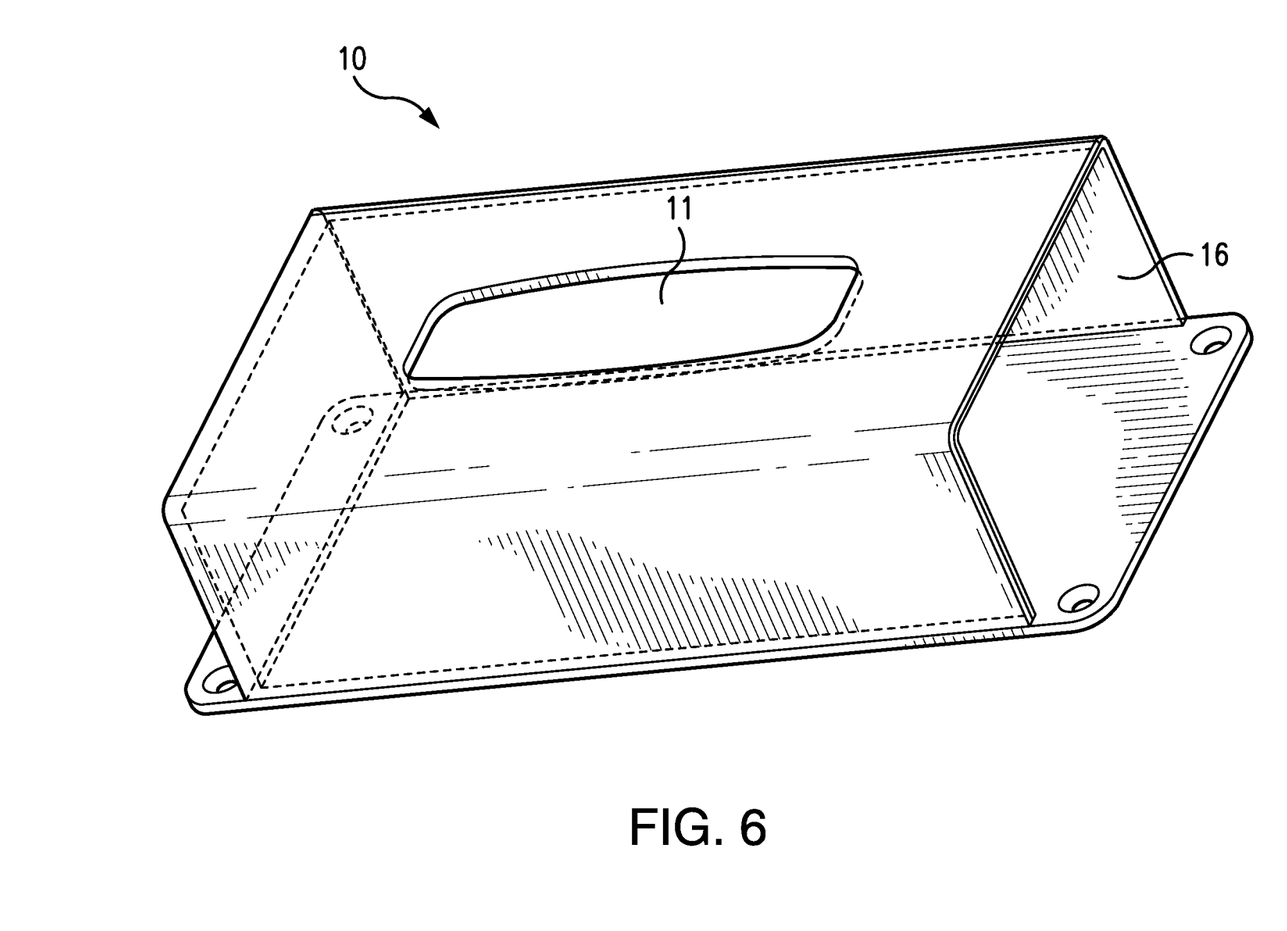
FIG. 6 is a perspective view of a dispenser box with a missing side wall through which a glove bag can be inserted into the box.

The foregoing method can employ several different types of dispenser boxes 10, as illustrated in FIGS. 2-6. The dispenser box 10 can provide access to its interior for insertion of glove bags 17 though a slidable lid 12, a hinged lid 14, a hinged side wall 15 or an open side 16. Each dispenser box 10 has at least one box aperture 11, through which disposable gloves can be pulled out of a glove bag 17 within the box 10. The box apertures 11 can also serve to allow glove bag labels 21 to be viewed. Alternately, a pair of cooperating tracks 13 can be provided on the lid 12 of the dispenser box 10 to enable insertion of a detachable bag label 21, as shown in FIG. 3.

Figure 7:
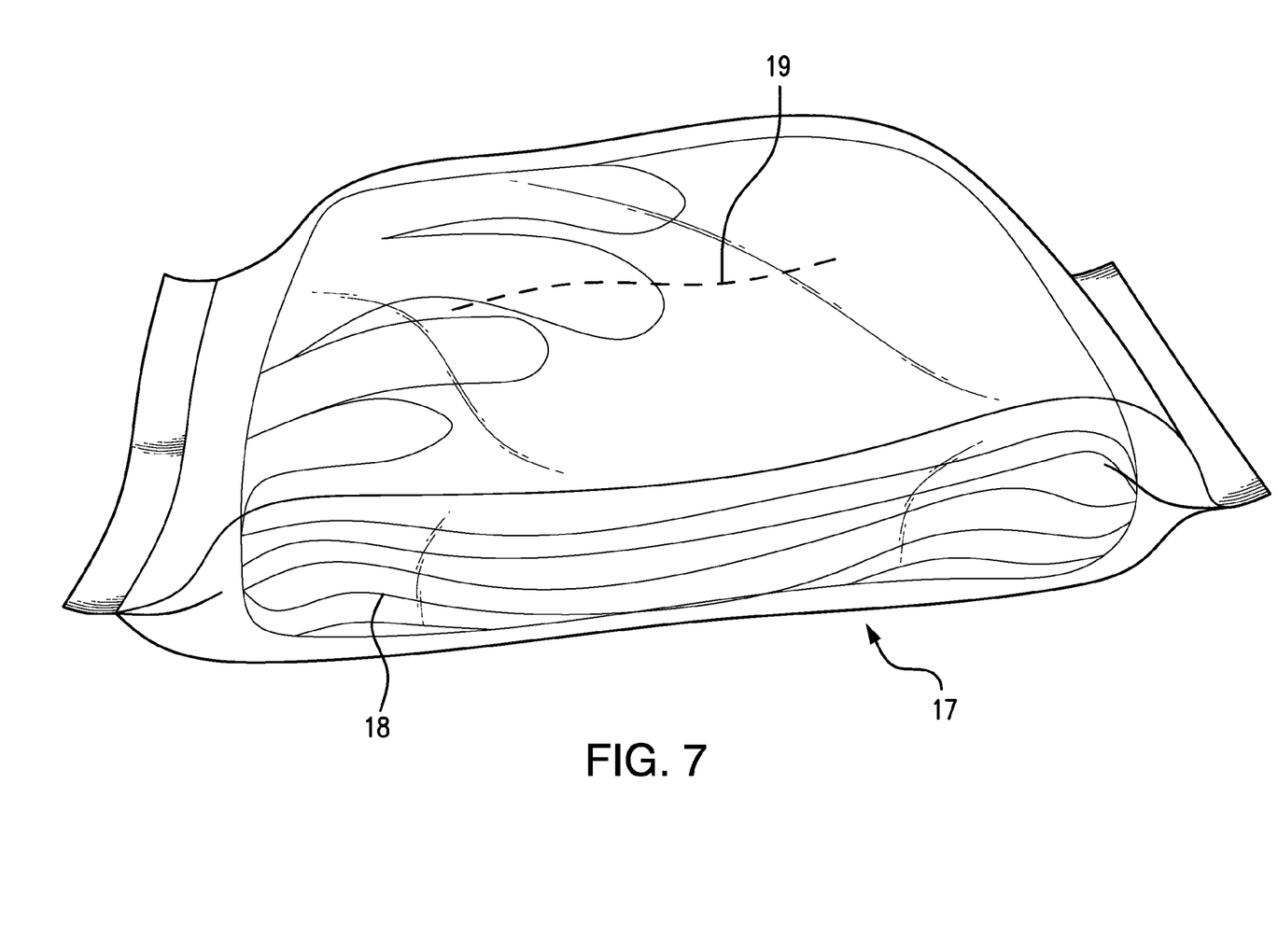
FIG. 7 is a perspective view of a glove bag having a perforated slit and containing a stacked bag allotment of disposable gloves.
Figure 8:
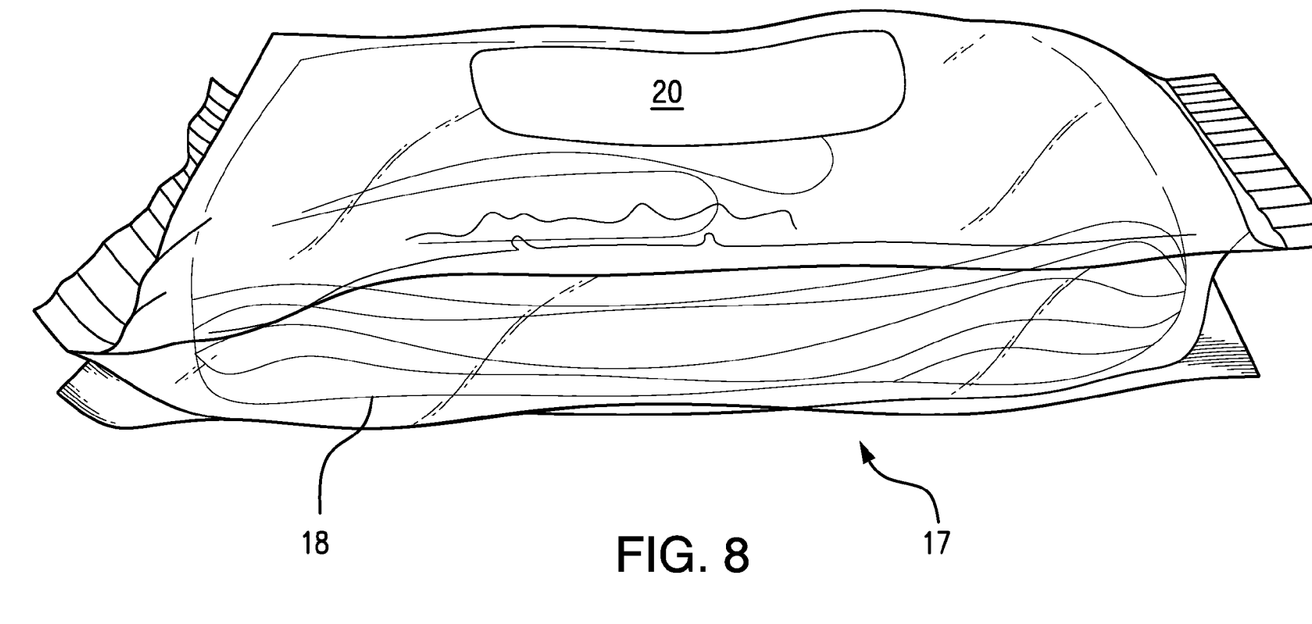
FIG. 8 is a perspective view of a glove bag having a peel-back slit and containing a stacked bag allotment of disposable gloves.
Figure 9:
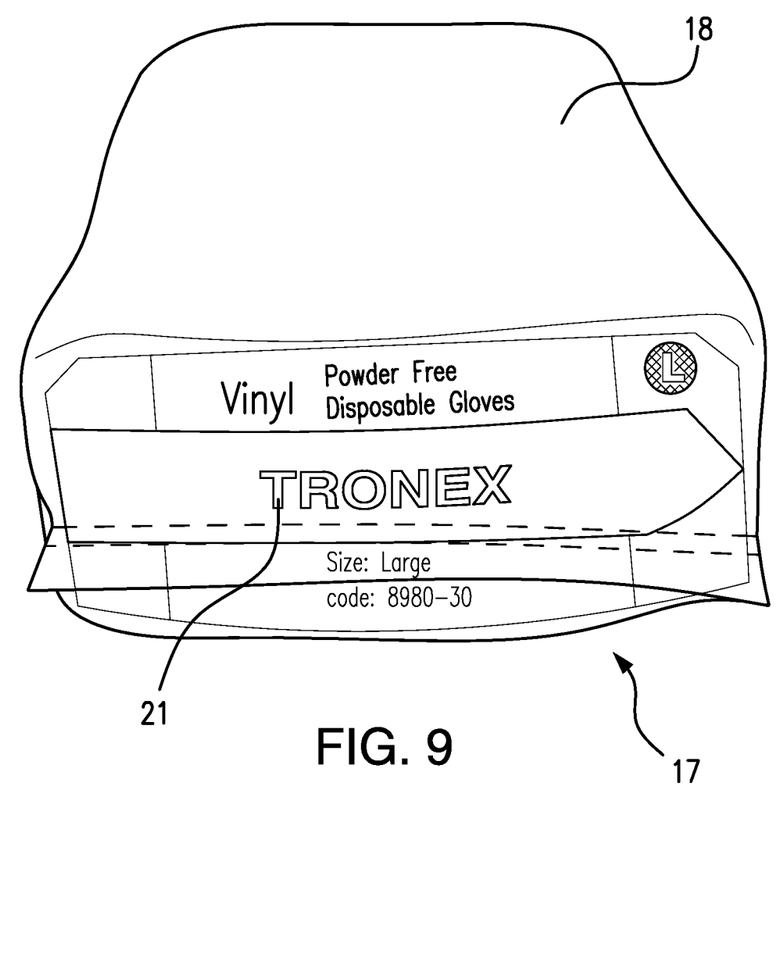
FIG. 9 is a perspective view of a glove bag having a bag label and containing a stacked bag allotment of disposable gloves.

Referring to FIGS. 7 and 8, each of the glove bags 17 contains a bag allotment stack 18 of disposable gloves, which are accessed through a bag slit, which can be, for example, a perforated slit 19, or an overlapping edge or a cut slit, or a peel-back slit 20. The stacking of the gloves of each bag allotment on top of one another is performed so that each successive glove has a random orientation with respect to the gloves above it and the gloves below it in the bag allotment stack 18.

Although the preferred embodiments of the present invention have been disclosed for illustrative purposes, those skilled in the art will appreciate that many additions, modifications and substitutions are possible, without departing from the scope and spirit of the present invention as defined by the accompanying claims.

What is claimed is:

1. A method of packaging and dispensing disposable gloves, comprising the following steps:
   (a) fabricating each of the disposable gloves by dipping a hand-shaped mold into a liquid resin of an elastomeric material, curing the resin on the mold, and then peeling off the glove, such that each glove has a three-dimensional form;
   (b) counting or weighing groups of the gloves so as to constitute multiple bag allotments, wherein each bag allotment contains a specified number of gloves, all of one specified material, size and thickness;
   (c) stacking the gloves of each bag allotment one on top of another, so as to constitute a bag allotment stack, wherein each bag allotment stack comprises a top glove, a bottom glove, and multiple successive gloves between the top glove and the bottom glove, and wherein the stacking of the gloves of each bag allotment on top of one another is performed so that each successive glove has a random orientation with respect to the gloves above it and the gloves below it in the bag allotment stack;
   (d) enclosing each bag allotment stack within a glove bag, wherein each glove bag comprises a flexible sheet or film of plastic defining an interior bag space, and wherein the interior bag space is accessible through one or more bag slits, which comprise narrow oblong openings, and wherein, within each glove bag, each successive glove has a random orientation with respect to the gloves above it and the gloves below it in the bag allotment stack;
   (e) placing each glove bag within a dispenser box, wherein each dispenser box comprises four or more substantially rectangular, rigid dispenser walls defining an interior dispenser space, and wherein the interior dispenser space is accessible through one or more box apertures in one or more of the dispenser walls;
   (f) aligning at least one of the bag slits with one of the box apertures;
   (g) pulling out the top glove from the glove bag through the bag slit and then through the aligned box aperture, and thereby exposing, by friction and entanglement between the gloves, a next successive glove at the bag slit; and
   (h) pulling each successive glove from the glove bag through the bag slit and then through the aligned box aperture, and thereby exposing, by friction and entanglement between the gloves, a next successive glove at the bag slit, until the bottom glove is pulled out and the glove bag is empty.

2. The method of claim 1, wherein each glove bag further comprises one or more bag labels, which contain descriptive information or specifications for the gloves in the bag allotment contained in the glove bag.

3. The method of claim 2, comprising the additional step of aligning one or more of the bag labels with one of the box apertures, so that the bag labels are visible through the aligned box aperture.

4. The method of claim 2, wherein one or more of the dispenser walls are substantially transparent walls, such that one or more of the bag labels are visible through the transparent walls.

5. The method of claim 2, wherein one or more of the bag labels are detachable from the glove bag, and wherein the method comprises the additional step of detaching one or more of the bag labels from the glove bag and attaching one or more of the glove labels to one or more of the dispenser walls, such that the attached bag labels are visible on the dispenser walls.

6. The method of any one of claims 1-5, wherein one or more of the dispenser walls are hingeably attached to the dispenser box, such that the hingeably attached dispenser walls can be lifted open so as to provide access to the interior dispenser space for insertion of the glove bag therein.

7. The method of any one of claims 1-5, wherein one or more of the dispenser walls are slidably attached to the dispenser box, such the slidably attached dispenser walls can be slid open so as to provide access to the interior dispenser space for insertion of the glove bag therein.

\* \* \* \* \*